(12) United States Patent
Almås

(10) Patent No.: US 10,246,327 B2
(45) Date of Patent: Apr. 2, 2019

(54) MULTI-CHAMBER HYPOCHLOROUS ACID DISPENSER

(71) Applicant: WIAB WATER INNOVATION AB, Malmo (SE)

(72) Inventor: Geir Hermod Almås, Oslo (NO)

(73) Assignee: WIAB WATER INNOVATION AB, Malmo (SE)

( * ) Notice: Subject to any disclaimer, the term of this patent is extended or adjusted under 35 U.S.C. 154(b) by 0 days.

(21) Appl. No.: 15/852,787

(22) Filed: Dec. 22, 2017

(65) Prior Publication Data

US 2018/0179059 A1 Jun. 28, 2018

Related U.S. Application Data

(60) Provisional application No. 62/438,182, filed on Dec. 22, 2016.

(51) Int. Cl.
| | |
|---|---|
| *B01J 19/24* | (2006.01) |
| *C01B 11/04* | (2006.01) |
| *A01N 59/00* | (2006.01) |
| *B05B 11/00* | (2006.01) |
| *B65D 81/32* | (2006.01) |

(52) U.S. Cl.
CPC .............. *C01B 11/04* (2013.01); *A01N 59/00* (2013.01); *B01J 19/24* (2013.01); *B01J 2219/24* (2013.01); *B05B 11/0081* (2013.01); *B05B 11/3057* (2013.01); *B65D 81/325* (2013.01); *B65D 81/3255* (2013.01)

(58) Field of Classification Search
CPC ........... C01B 11/04; A01N 59/00; B01J 19/24
USPC ....................................................... 422/187
See application file for complete search history.

(56) References Cited

U.S. PATENT DOCUMENTS

| | | | | |
|---|---|---|---|---|
| 5,398,846 | A * | 3/1995 | Corba ................. | B05B 11/0029 222/1 |
| 5,759,489 | A * | 6/1998 | Miura ....................... | A61L 2/18 134/22.11 |
| 5,944,223 | A * | 8/1999 | Klima ................. | B05B 11/0056 222/129 |

* cited by examiner

*Primary Examiner* — Huy Tram Nguyen
(74) *Attorney, Agent, or Firm* — Brown Rudnick LLP; Thomas C. Meyers

(57) ABSTRACT

The invention provides a skin disinfectant for treating skin with eczema, preventing bacterial proliferation, and removing biofilm. Compositions of the invention include hypochlorous acid, acetic acid, water, and one or more additives or excipients. The formulation process removes metal ions, reduces ionic strength, controls pH, and reduces exposure to air, thus improving stability and lengthening shelf-life.

21 Claims, 4 Drawing Sheets

MULTI-CHAMBER HYPOCHLOROUS ACID DISPENSER

RELATED APPLICATIONS

This application claims priority to and the benefit of U.S. Provisional Patent Application Ser. No. 62/438182, filed Dec. 22, 2016, the content of which is incorporated by reference herein in its entirety.

FIELD OF THE INVENTION

The invention generally relates to multi-chambered containers for producing, storing, and dispensing hypocholorous acid.

BACKGROUND

Hypochlorous acid (HOCl) is a weak acid that is known to rapidly inactivate bacteria, algae, fungus, and other organics, making it an effective agent across a broad range of microorganisms. Additionally, since hypochlorous acid is a weak acid and since people naturally produce certain compounds that allow them to tolerate hypochlorous acid, it is generally not harmful to people. Due to the combination of its biocide properties and its safety profile, hypochlorous acid has been found to have many beneficial uses across many different industries, such as the medical, foodservice, food retail, agricultural, wound care, laboratory, hospitality, dental, or floral industries.

Hypochlorous acid is formed when chlorine dissolves in water. One manufacturing method involves the electrochemical activation of a saturated salt solution (e.g., brine) to form HOCl. Another production method involves the disproportionation of chlorine gas in alkaline solutions.

A problem with hypochlorous acid produced by these methods is that it is highly unstable, and over a short period of time (e.g., a few hours to a couple of weeks) the hypochlorous acid will degrade. The distribution of chloric compounds in aqueous solution is known to be a function of pH. As the pH of a solution containing hypochlorous acid becomes more acidic (e.g., pH below 3), chlorine gas is formed. As the pH of a solution containing hypochlorous acid becomes more basic (e.g., pH above 8) hypochlorite anions (OCl—; i.e., bleach) are formed, which are also toxic to people. Thus, while being an effective biocide, the use of hypochlorous acid has been limited by the need for onsite generation and the challenge of maintaining stability in storage.

SUMMARY

The present invention provides a multi-chambered container for preparation, dispensing, and long term, stable storage of hypochlorous acid. Containers of the invention provide a two-fold benefit: one allowing simple, on-site preparation of hypochlorous acid, thereby avoiding some requirements for long-term stability by storing the hypochlorous acid in its more stable component parts until time for use; furthermore, the air-free nature of the container and the use of buffering agents provides long-term stability for hypochlorous acid once it has been prepared in the container. Containers described herein may have a number of compartments or chambers separately containing the components required to produce hypochlorous acid. One compartment can contain a compound that generates a proton (H+) in water and another compartment may contain a compound that generates a hypochlorite anion (OCl—) in water. One or both of these compartments may also contain water. The compartments are separated from each other but connected to a third compartment that may contain water so that the two compounds can enter the third compartment together and produce hypochlorous acid. One way valves allow passage of the compounds from the first and second compartments into the third compartment but do not allow reverse flow from the third compartment to the compound containing compartments. Containers may comprise a fourth compartment containing water.

Hypochlorous acid of the present disclosure is useful as a disinfectant that is effective for, among other things, treating surfaces, instruments, and biological uses, preventing bacterial proliferation, combating antimicrobial resistance, preventing biofilm formation, and removing biofilm where it already exists. The invention uses hypochlorous acid (HOCl) and acetic acid as a disinfectant rather than alcohol. HOCl has a high oxidative capacity, which makes it an ideal disinfectant. However, HOCl is also an unstable compound. That limitation has made prior art HOCl-based disinfectants inadequate.

To present invention provides highly-effective but stable HOCl and acetic acid compositions. Hypochlorous acid compositions of the invention are substantially free of chloride or metal ions. Compositions of the invention have a balanced pH within a range of about 3.7 to 5.8. The disclosed compositions provide a stable HOCl based disinfectant with a long shelf-life that is increased through separate component storage in containers of the invention, previously unavailable in the art. Other additives and excipients may be included in the composition, which further enhance stability. It should be understood that not all common off-the-shelf additives are compatible because they may degrade the active compound to such an extent that the product loses its activity.

Aspects of the invention include a system for storing and producing hypochlorous acid (HOCl). The system may comprise a container from which air has been purged, the container comprising a first compartment, a second compartment, and a third compartment, wherein the first compartment contains a compound that generates a hypochlorite anion (OCl—) in the presence of water and the second compartment contains a compound that generates a proton (H+) in the presence of water. The system may further comprise a first one-way valve that permits fluid flow from the first compartment to the third compartment and a second one-way valve that permits fluid flow from the second compartment to the third compartment.

In various embodiments, the first compartment, the second compartment, or the third compartment may contain water. The first, second, or third compartments may contain at least one buffering agent. The water may have a buffering capacity from about pH 3.5 to about pH 9.0. The buffering agent may include an acetic buffer or phosphate buffer. The first compartment may comprise walls of an opaque material.

In certain embodiments, the first and second one-way valves may be configured to permit flow from the first and second compartments into the third compartment in response to an increase in pressure within the first and second compartments. The first and second one-way valves may be configured to permit flow from the first and second compartments into the third compartment at a defined ratio in response to an increase in pressure within the first and second compartments.

Systems of the invention may further comprise a member configured to increase pressure within the first and second compartments upon user manipulation. The first and second compartments may comprise walls of a flexible material configured to allow an increase in internal pressure of the first and second compartments in response to a force administered to an outside surface of the first and second compartments. The system may further comprise a third one-way valve that permits fluid flow from the third compartment to an exterior of the container. The third compartment may be configured to direct its contents to the exterior of the container in response to an increase in pressure within the third compartment.

In certain embodiments, systems may comprise a member configured to increase pressure within the third compartment upon user manipulation. The third compartment may comprise walls of a flexible material configured to allow an increase in internal pressure of the third compartment in response to a force administered to an outside surface of the third compartment. The compound that generates a proton may comprise an organic acid. The organic acid may comprise acetic acid. The compound that generates a hypochlorite anion (OCl—) may comprise sodium hypochlorite (NaOCl), Mg(OCl)2, or Ca(OCl)2. In certain embodiments, systems may be configured to produce hypochlorous acid (HOCl) having a pH from about 4.5 to about 7.5 in the third compartment after introduction into the third compartment of the compound that generates a hypochlorite anion and the compound that generates a proton from the first and second compartments respectively. Systems of the invention may further comprise a fourth compartment coupled to the third compartment by a fourth one-way valve that permits fluid flow from the fourth compartment to the third compartment, the fourth compartment comprising water. The container may be a spray bottle.

DETAILED DESCRIPTION

Figure 1:
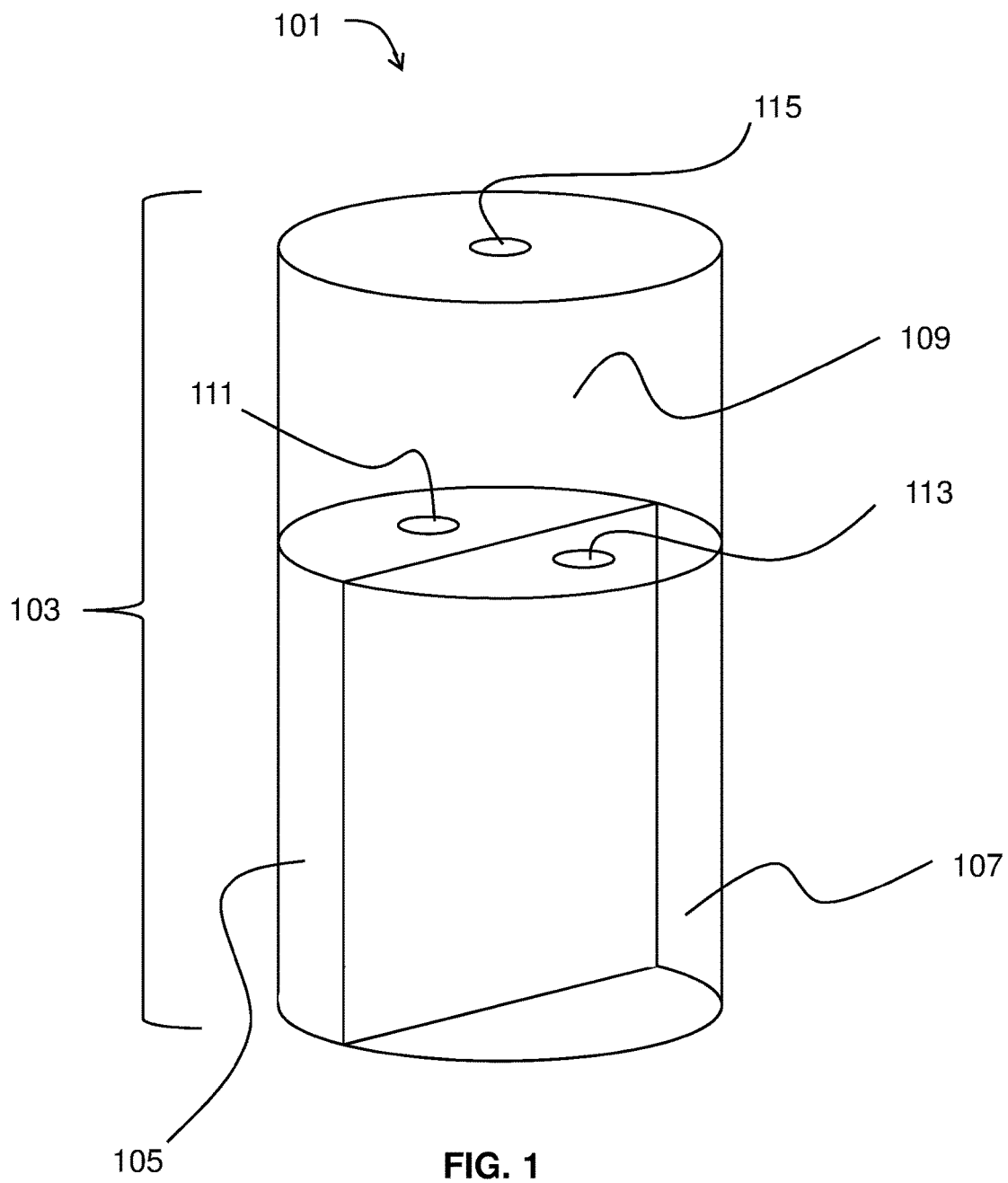
FIG. 1 shows a system and container according to certain embodiments.

The present invention recognizes the disinfecting power of HOCl and provides a storage and mixing container that, along with the specific formulations described herein, allow for long-term stable storage of hypochlorous acid components as well as easy on-site mixing as needed. Hypochlorous acid is a reactive species due to its oxidative capacity. In aqueous solution, HOCl is involved in chemical equilibria with other reactants and products. The multiple equilibria can be complex, and in order to control or kinetically delay the breakdown of HOCl, the invention controls several factors in the formulation process. Furthermore, in order to prolong stability, systems of the invention provide multi-chambered containers that can keep separate the components that are used to produce HOCl compositions of the invention and allow for on-site and on-demand preparation. Additionally, once mixed, the present invention stabilizes the HOCl solution by regulating pH, removing metal ions and chloride ions, and reducing ionic strength. Those factors are controlled using a process that combines ion exchange and mixing in a substantially or completely air-free environment such as an air-free multi-compartment container made, for example, by degassing through reduced pressure. The resulting composition retains the reactive advantages of hypochlorous acid but has increased stability, which makes it useful for both the consumer and healthcare provider markets. The storage containers are configured to be air-free as well as control other variables, such as UV exposure.

Hypochlorous Acid Production

Compositions and methods of the invention take advantage of the protonation of the hypochlorite ion (OCl$^-$). Using HCl and NaOCl as an example, the protonation is accomplished by introducing an acid (e.g., HCl) to the solution, which results in the following reaction: HCl(aq)+NaOCl(aq)↔HOCl(aq)+NaCl(aq).

The hypochlorous acid in aqueous solution partially dissociates into the anion hypochlorite (OCl$^-$). Thus in aqueous solution there is always an equilibrium between the hypochlorous acid and the anion (OCl$^-$). That equilibrium is pH dependent and at higher pH the anion dominates. In aqueous solution, hypochlorous acid, is also in equilibrium with other chlorine species, in particular chlorine gas, Cl$_2$, and various chlorine oxides. At acidic pH, chlorine gases become increasingly dominant while at neutral pH the solution is dominated by hypochlorous acid. Thus, it is preferable to control exposure to air and pH in the production of hypochlorous acid.

Any compound that produces a hypochlorite anion (OCl$^-$) in water may be used with methods of the invention. Exemplary compounds include NaOCl and Ca(OCl)$_2$. In particular embodiments, the compound is NaOCl. Any compound that produces a proton (H$^+$) in water may be used with methods of the invention. Exemplary compounds are acids, such as acetic acid, HCl and H$_2$SO$_4$. In particular embodiments, the compound is HCl. In preferred embodiments, the compound is an organic acid such as acetic acid. Acetic acid is a weaker acid than HCl with a preferred pKa. It is more able to maintain the preferred pH level.

FIG. 1 shows an exemplary system 101 and container 103. The container 103, from which air has been purged, comprises a first compartment 105 containing a compound that generates a hypochlorite ion (OCl—) in the presence of water. Examples of such compounds are discussed above. The container 103 further comprises a second compartment 107 containing a compound that generates a proton (H+) in the presence of water. Examples of such compounds, including organic acids, are discussed above. The first 105 and second 107 compartments are separate from each other but connected to a third compartment 109 by first 111 and second 113 one-way valves respectively. The first one-way vale 111 permits the contents of the first compartment 105 to enter the third compartment 109 in response to an increase in pressure within the first compartment 105 but does not permit reverse flow from the third compartment 111 into the first compartment 105. The second one-way vale 113 permits the contents of the second compartment 107 to enter the third compartment 109 in response to an increase in pressure within the second compartment 107 but does not permit reverse flow from the third compartment 111 into the second compartment 107.

The third compartment 109 includes a third one-way valve 115 that allows the contents of the third compartment 109 to be dispensed from the container 103 in response to an increase in pressure within the third compartment 109 but does not allow air to enter the third compartment 109 from the exterior of the container 103.

Figure 4:
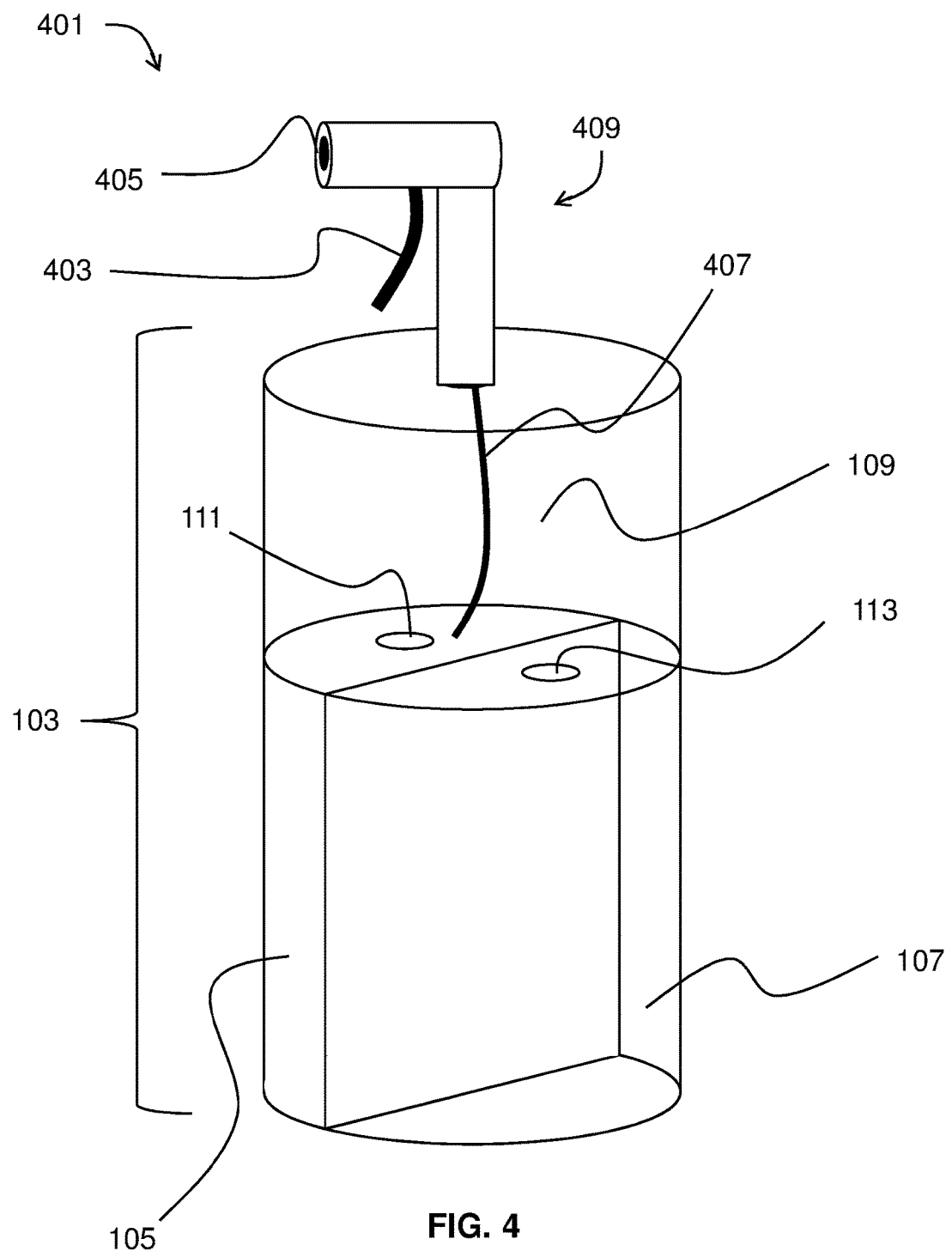
FIG. 4 shows a multi-compartment spray bottle according to certain embodiments.

The container 103 may be part of a spray bottle 401 as shown in FIG. 4. The third compartment 109 may have a pump 409 actuated by a trigger 403 and operable to draw fluid from within the third compartment 109 through a tube 407 and expel the drawn fluid through a nozzle 405. The third compartment may be pressurized and its contents may be dispensed by operating a one-way valve to allow some of the pressure to release along with some of the fluid contents of the third compartment. In certain embodiments, the internal pressure may be provided by pressurized gas propellant. Pressure may be provided by a pump that may draw gas from a separate container as opposed to the outside environment such that the composition of the pressurizing gas can be controlled to maintain stability in the HOCl. Producing and storing hypochlorous acid in an air-free environment and under pressure allows for the production of HOCl that does not interact with gases in the air (e.g., oxygen and $CO_2$) that may destabilize the produced HOCl.

The container may be constructed from any inert material such that material from the container walls does not become involved with the reaction occurring within container. Exemplary materials include PVC-U.

Figure 3:
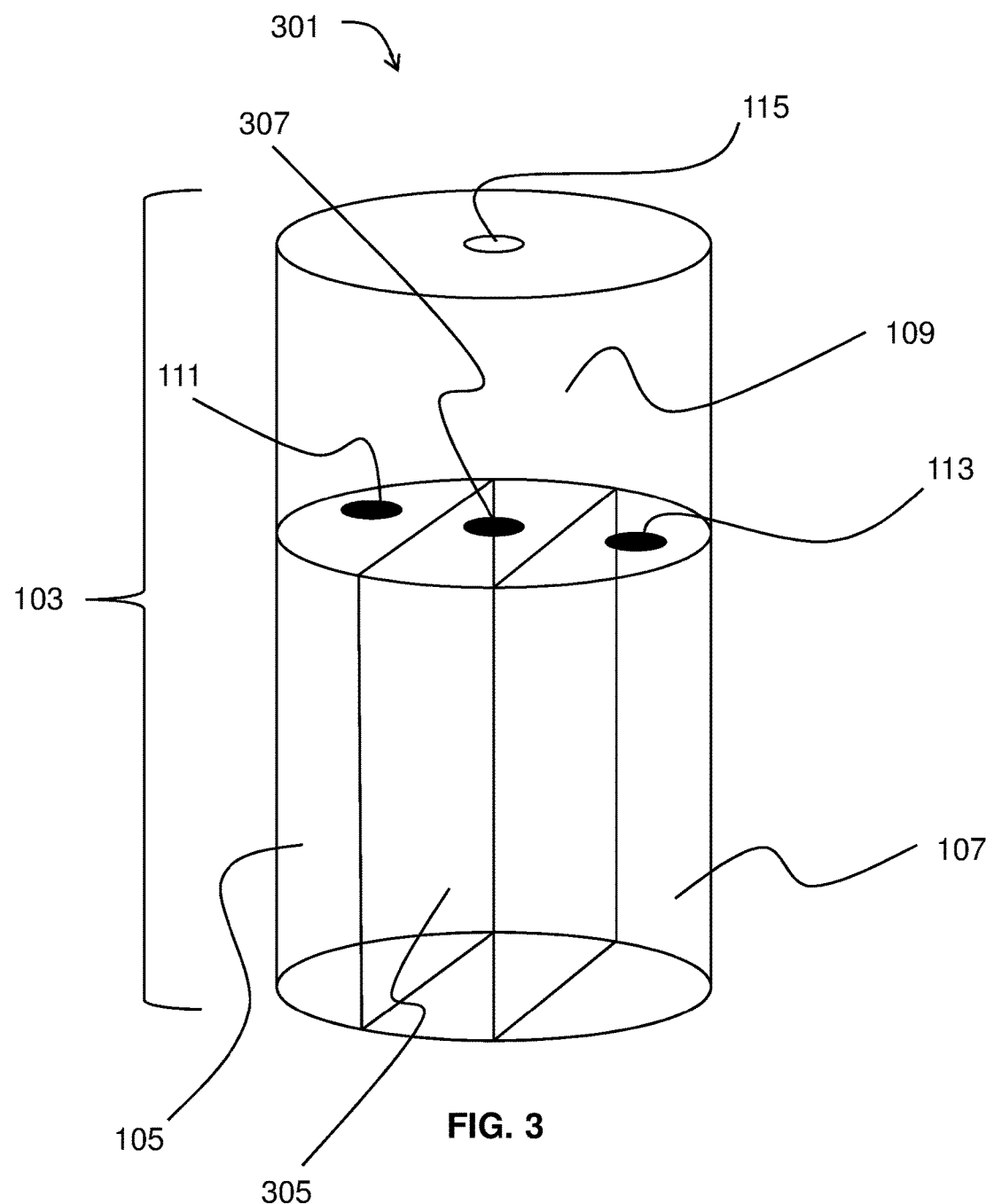
FIG. 3 shows a container having four compartments.

FIG. 3 shows a system 301 of the invention that comprises a fourth compartment 305 separate from the first 105 and second 107 compartments and in fluid communication with the third compartment 109 by way of a fourth one-way valve 307 that allows fluid to flow from the fourth compartment 305 to the third compartment 109 in response to an increase in pressure in the fourth compartment 305 but does not allow reverse flow into the fourth compartment 305 from the third compartment 109.

In various embodiments the first, second, third, or fourth compartments, or any combination thereof may contain water such that the compounds in the first and second compartments may produce a hypochlorite ion ($OCl^-$) and a proton ($H^+$) respectively. The compounds may be stored along with water in their respective compartments or may be introduced into water already present in the third compartment. In certain embodiments, water may be added to the third compartment from a separate fourth compartment along with the compounds from the first and second compartments. In certain embodiments tap water is used. In other embodiments, deionized water with the addition of one or more known buffering agents is used. Examples of buffer include phosphate buffer and acetic acid buffer. For greater control and consistency, using formulated deionized water may be preferable to using tap water because tap water can change between locations and also over time. Additionally, using deionized water with known additives ensures a stable pH of the incoming water flow.

Because compounds of the invention may be light-sensitive, the container or one or more compartments therein may be made of an opaque material that limits UV exposure for the contents therein. In certain embodiments, the first compartment containing the $OCl^-$ generating compound and/or the third compartment may be constructed of an opaque material or coated, treated, or covered with a material that limits or blocks UV light.

As noted earlier, the first, second, third, and fourth one-way valves may be operable to permit fluid to pass from one compartment to the other in response to an increase in pressure in the compartment from which the fluid is passing. In certain embodiments, the first and second one-way valves allow fluid to pass from the first and second compartments respectively in response to an increase in pressure therein. The walls of any of the compartments and/or the entire container, may be constructed of a flexible material such as a plastic that is configured to elastically deform in response to pressure on the outside of the container or individual compartments thereof. Accordingly, a user may squeeze the container or compartments by hand in order to increase pressure in any of the compartments and thereby force fluid from, for example, the first and second compartments into the third compartments or the third compartment to the outside of the container. The valves or compartments may be sized an configured such that compounds within the first, second, and/or fourth compartment are introduced into the third compartment at a prescribed ratio to one another.

Figure 2:
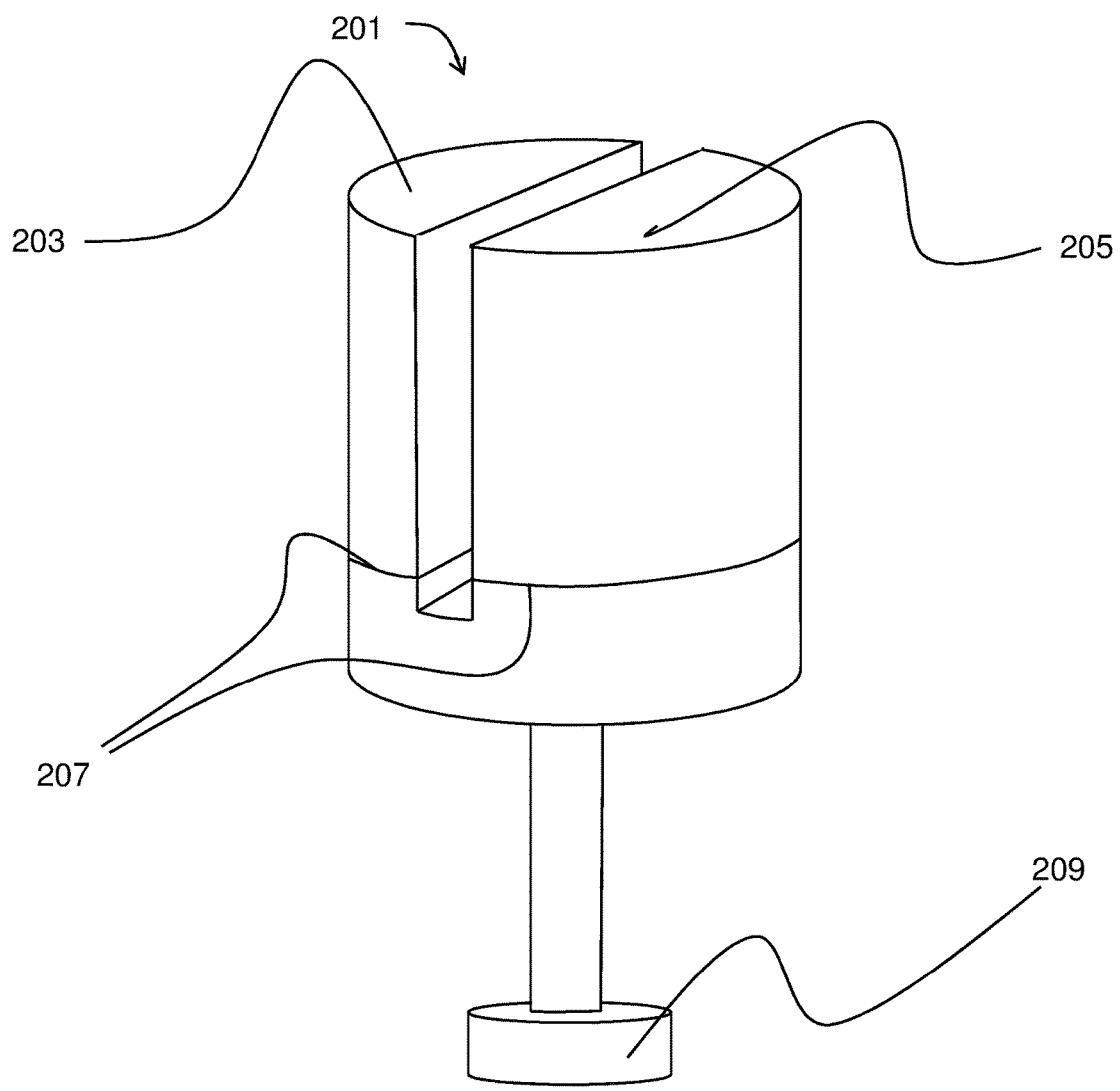
FIG. 2 shows a member for increasing pressure in the first and second compartments.

In certain embodiments, the container may comprise a member 201 such as depicted in FIG. 2. The member 201 is shaped and sized so that it fits within the bottom of the container with a first section 203 fitting within the first compartment and a second section 205 fitting within the second compartment. The member 201 comprises gaskets 207 that form an air tight seal with the inside walls of the first and second compartments. The first 203 and second 205 sections of the member 201 are configured to be slideably engaged with the inner walls of the first and second compartments and to form bottom walls thereof. The member may further comprise a plunger 209 that, when force is applied to it, moves the member 201 further into the first and second compartments, decreasing the interior volume of the compartments and increasing their internal pressure accordingly. In certain embodiments, the compartments and sections 203, 205 of the member 201 may be sized so that, upon application of a force to the plunger 209, compounds within the first and second compartments are passed through the first and second valves into the third compartments at a prescribed or defined ratio. For example, if the first compartment and the upper surface of the first section 203 of the member 201 have ½ the cross-sectional area of the second compartment and upper surface of the second section 205 of the member 201, then for any given upward movement of the plunger 209, the volume in the first compartment would decrease by an amount ½ as much as the decrease in volume of the second compartment. Accordingly the volume of fluid displaced into the third compartment from the first compartment would be half of the volume of fluid displaced from the second compartment. Furthermore, the container may be configured (e.g., pressurization of the third compartment, sensitivity of the third one-way valve, and wall stiffness in the third compartment) such that an increase in pressure in the first and second compartments using the member 201 will force fluid into the third compartment, increasing pressure therein, and causing the fluid contents of the third compartment to pass through the third one-way valve and be dispensed for use.

Containers may comprise a pH meter and/or conductivity measuring device. These devices measure the concentration (ppm), purity, and pH of the HOCl being produced and provide feedback on stability of the produced HOCl.

The anion and ion generating compounds are placed into the first and second compartments in an air-free manner. Placing liquids into a bottle in an air-free manner is known in the art. An exemplary method includes placing an inflatable vessel (such as a balloon) into a compartments. The inflatable vessel is connected directly to a feed line and the compounds are pumped directed into the inflatable vessel in the compartments without ever being exposed to air. Another method involves filling the compartments under vacuum. Another air-free filling method involves filling the compartments in an environment of an inert gas that does not interact with the HOCl or its constituent components, such as an argon or nitrogen environment.

The produced hypochlorous acid is air-free and will have a pH from about 4.5 to about 7.5. However, the pH of the produced HOCl can be adjusted post production process by adding either acid (e.g., HAc) or alkali (e.g., NaOH) to the produced hypochlorous acid. Containers may include means for introducing these adjusting compounds, such as injection ports or additional acid or alkali containing compartments. For example, a pH of between about 4.5 and about 7 is particularly suitable for the application of reprocessing heat sensitive medical instruments. Other applications, such as its use in non-medical environments, for example as in the processing of poultry and fish and general agricultural and petrochemical uses, the breaking down of bacterial biofilm and water treatment, may demand different pH levels. Containers, buffering agents, and component concentrations therein may be configured for different pH levels and intended for different fields of use.

Product Stability

The invention controls several factors that contribute to the stability of the final product. Those factors include air exposure, pH, buffering capacity, ion concentration, the presence of metal ions, and packaging that blocks UV light exposure. As will be evident from the following discussion, those factors are interrelated in a variety of ways.

Protecting the composition from exposure to air contributes to HOCl stability. Methods and devices for producing HOCl in an air-free environment are described in US 2013/0216628 and US 2013/0215709, both of which are hereby incorporated by reference in their entirety. One reason that producing HOCl in an air-free environment, such as an environment degassed through reduced pressure, helps stability is that it reduces or avoids the presence of carbon dioxide ($CO_2$), which is present in air. $CO_2$ dissolves readily in water (approximately 1.5 g/L). Furthermore, the equilibrium between air and water is established within minutes. When dissolved $CO_2$ reacts with water, it forms $H_2CO_3$, which is an acid. $H_2CO_3$ deprotonates in water, releasing $H_3O^+$, which decreases the pH of the water.

$CO_2$ can be removed from a water solution by heating or by purging the water with $N_{2(g)}$. Purging replaces the $CO_2$ with $N_2$. But that does not fully solve the problem if the solution is still exposed to air. Since the solubility of $CO_2$ in water is high, new $CO_2$ will quickly be re-dissolved and replace the $N_2$ unless the water is protected from interactions with air.

In addition to $CO_2$, oxygen is another reactive molecule present in air that dissolves in water, although not as fast and not to the same degree as $CO_2$. Like $CO_2$, oxygen can be removed from a water solution by heating or by purging $N_{2(g)}$ through the water to replace $O_2$ with $N_2$. In a solution of HOCl, $O_2$ can react with the hypochlorous ion $ClO^-$ and form the chlorate ion $ClO_3^-$. That reaction is pH dependent, which is one reason that pH control is an important factor. The reaction does not proceed to an appreciable extent at lower pH, such as approximately 4.0.

There are additional reasons why the present invention seeks to control pH. Several of the equilibria involved in a mixture of HOCl in water are pH dependent, which means that controlling the pH is extremely important. The pH must be controlled at all stages: during production of the HOCl in the container and during storage of the formulated product.

HOCl in water is in equilibrium with the less potent $OCl^-$ ion. At higher (more basic) pH, the $OCl^-$ ion dominates. Therefore, lower pH, where the more potent HOCl dominates yields a superior product. At a pH around 4.0 to 5.0, there will not be much production of $Cl_{2(g)}$.

To achieve that optimal pH, the invention uses NaOH and acetic acid to titrate the water used in the various compartments to the right pH. The choice of acetic acid is important because it has a pKa of 4.76, and so its maximum buffering capacity is at pH 4.76. Acetic acid is therefore a good choice for titrating the solution to create a product that is dominated by HOCl rather than $OCl^-$.

Ionic strength is another important factor in the stability of HOCl. Ionic strength is correlated with the total concentration of ions in the solution. For HOCl, it has been shown that higher ionic strength, which can result from the use of buffers that add ions to the solution, actually destabilizes the HOCl (see Adam et al., Inorg. Chem. 1992, 31, 3534-41). Thus not all buffers increase the stability of the HOCl. Starting with an optimum pH and using an acid with the right pKa (such as acetic acid, as described above) prevents the need to titrate with a surplus of ions. The combination of NaOH and HAc to make a HAc-NaAc buffer has been found to provide better stability than using NaOH and HCl. The combination of NaOH and HCl increases ionic strength and also increases chloride ions, which hurt stability as well. It is also better than a phosphate buffer system that was found to have worse stability.

In certain embodiments, the water in the compartments has a pH of 6 before titration. If the water has been in contact with air such that $CO_2$ has dissolved, the pH can be lower than 6. In that case, more NaOH is added, leading to a higher total number of ions in the solution, which destabilizes the product.

Various factors go into which buffer to choose. A buffer can stabilize the pH (which has a positive effect on product stability) and at the same time increase the ionic strength (which has a negative effect). Different buffers will not have the same positive effect (depending on their pKa), or the same negative effect (mono-, di-, and trivalent ions have different impact on ionic strength).

Another stability factor that the invention controls is the presence of metal ions in the water and solutions used. Metal ions such as $Fe^{2+}$, $Fe^{3+}$, and $Mn^{2+}$ are a source of destabilization. Metal ions are not removed by purging with $N_2$ or heating the water. In the pharmaceutical industry, EDTA is used in order to capture or chelate the metal ions. That ensures that they do not initiate a catalytic breakdown. However, adding EDTA to the solution is not desirable for HOCl because the EDTA would be oxidized, resulting in production of toxic chlorine gas, $Cl_{2(g)}$. The metal ions are present in their charged ionic form, and so the invention uses an ion exchange method to remove them.

The ion exchange removes metal ions and $CO_2$ (through the removal of $CO_3^{2-}$ and $HCO_3^-$ ions) and assures a near neutral pH of the water used in the container. That approach reduces the ionic strength of the final product. Protecting the composition from air by mixing in an air-free environment helps to further stabilize pH since it protects the water from $CO^2$. The water can be run through the ion exchange mass twice, which helps to remove $CO_3^{2-}$ and $HCO_3^+$ as well as removing more metal ions in order to prevent catalytic reactions.

Prior art methods of only using $N_{2(g)}$ to remove gas such as oxygen and carbon dioxide fail to reduce the number of metal ions and also fail to prevent interaction with air. Additionally, those methods do not assure that the incoming process water has the correct pH to reduce the final ionic strength of the product.

When HOCl is produced in the presence of air, the result is bad stability, regardless of whether one or two ion exchange cycles were used. Protecting the solution from air improves stability. The air-tight in-container process in combination with two ion exchange cycles provides a significantly higher stability than only one ion exchange cycle. That result confirms that control of the reactions and equilibria discussed above is an important factor in stability of the composition.

Disinfectant Formulation

The improved stability of HOCl achieved by the present invention makes it much more useful as a disinfectant than previously possible. The disinfectant properties of HOCl are generally known. HOCl is a weak acid that is known to rapidly inactivate bacteria, spores, viruses, algae, fungi, and other organics, making it an effective agent for across a broad range of microorganisms. Humans produce certain compounds such as taurine that allow them to tolerate hypochlorous acid, and so it is a safe disinfectant for use on skin. But HOCl produced by traditional methods is highly unstable, and over a short period of time (e.g., a few hours to a couple of weeks) the hypochlorous acid degrades.

Containers of the invention address these issues by providing for on-site preparation in a single container that produces a more stable HOCl product. The formulation can be titrated with NaOH and HAc to obtain a pH of about 4.6-4.7.

In addition to buffering the product during storage and after application, acetic acid also has the advantage of improving the sporicidal effect by 40% compared to other acids used for protonization of HOCl.

As discussed above, pH is an important factor that is controlled throughout the production process within the container. When pH is too low, chlorine gas will evolve which is undesirable. When pH is too high (like most other HOCl products on the market) then the product equilibrium is dominated by the less-potent $OCl^-$ ions. Formulations of the present invention can have a pH in the range of 3.0 to 8.0, although formulations at the higher end of that range will be much less potent than a formulation at the preferred pH of between 4.0 and 5.0, and even more preferably 4.76. Acetic acid has a buffering capacity between approximately 3.7 and 5.8.

Formulations of the present invention may include an additive or excipient. Excipients provide different qualities to the final product, such as a desired viscosity for pumping and handling. Excipients may include a thickening agent and/or a chelator. Excipients may include, for example, inorganic thickeners such as colloidal silica, synthetic clay materials, or the product sold under the trademark LAPONITE by BYK Additives (Cheshire, UK). Excipients may additionally or alternatively include EDTA, polyethylene glycol, polysorbate, glycerol, acrylate copolymer, essential oils, buffers, cellulose derivatives, or xanthan gum.

Additives can also be added for a hydrating effect, which is desirable for topical uses. Additives can also be added for improving fragrance, cleansing, preservation, or to impart other qualities on the final product, which may take the form of a cream, gel, lotion, balm, or other topical ointment.

Containers of the invention may be used to prepare and dispense hand disinfectant products. Below many additives are discussed that are commonly used in hand disinfectant products known in the art. Additives may be included in any of the compartments including held in separate compartments from the compounds or water discussed above for separate mixing before dispensing. Because HOCl is an oxidative species the choice of additive is not trivial. Some additives should not be used with HOCl at the preferred pH levels. The list of additives discussed below includes common excipients used in hand disinfectant products or other similar product types, and is a non-comprehensive list of additives for use with the invention.

Some of the excipients discussed are more desirable than others, based partly on their susceptibility to oxidation, which affects shelf-life. Even less desirable excipients can still be used, partly depending on other factors such as molecular variability (cross-linkers in certain polymers, for example), the presence of metal ions (glycerol in particular), and chemical origin (polyethylene glycol-based surfactants or sugar-based surfactants, for example).

With any of the excipients, oxidation will occur, but some will provide a longer time horizon. Even the excipients discussed below that have a relatively short time horizon would still provide usable shelf-life for the product, particularly because HOCl in this formulation is in a very low concentration.

One excipient commonly used with topical formulations is ethylenediaminetetraacetic acid (EDTA). EDTA is the chelating agent commonly used to diminish the catalytic reactivity of trace metal ions in purified water. In the presence of HOCl, EDTA will be oxidized to glyoxylic acid and formaldehyde, and the HOCl will be reduced to chlorine gas. The latter is known to happen when EDTA is added to a concentrated solution of $HOCl/OCl^-$. The kinetics will be slower at the relatively low concentrations of HOCl in the preferred formulation of the invention, but nevertheless it is a degrading combination. Thus, other excipients may be preferable to EDTA. In preferred embodiments of the invention, metal ions are removed through the proprietary ion exchange process rather than by using EDTA.

Polyethylene glycol (PEG) is another common excipient. However, PEG is very sensitive to oxidation and will be degraded by HOCl, resulting in oxidation products such as aldehydes, ketones, acids and dioxolanes, as well as a strong odor and pH destabilization.

Another excipient frequently found in hand disinfectants is any of a number of common essential oils. These will be degraded through oxidation (see, e.g., Turek & Stintzing, 2014, "Stability of Essential Oils: A Review," Comprehensive Reviews in Food Science and Food Safety). The result may be degradation products that lead to bad odors and pH destabilization, like with PEG.

Buffers are also potential excipients. As discussed above, many buffer systems increase the ionic strength of the solution, creating a destabilizing effect. A buffer system of NaOH and acetic acid is preferred by the invention.

Polysorbates (Polysorbate 20 and Polysorbate 80) are also common additives, but those too are prone to oxidative degradation (see Borisov et al. "Oxidative Degradation of Polysorbate Surfactants Studied by Liquid Chromatography—Mass Spectrometry" J. Pharm. Sci. 194 (3), 2015).

Polymers, such as any type of acrylate copolymer, which are well known to those of skill in the art, can function well in the formulation of the invention. Acrylate copolymers are homo- and co-polymers of acrylic acid cross-linked with a polyalkenyl polyether. Acrylate copolymers come with a variety in graft density. They vary in terms of their ability to oxidize and how many grafted chains there are per polymer. One possible cross-linker is pentaerytritol which is very stable, and so it is a good choice for use with the present invention. Polyacrylic acid (PAA) polymers that are known to stabilize formulations of $H_2O_2$ can be used with the present invention. (see Schmucker-Castner & Desai, 1999, "Rheology Modification of Hydrogen Peroxide Based Applications Using A Cross-linked PAA polymer," Int J Cosmet Sci 21 (5):313-25).

Many other excipients may be used. Inorganic thickeners such as silica and laponite (a synthetic clay material related to silica) may provide better results. For example, silica works well to create a gel and to retain the concentrations of HOCl. Glycerol, or glycerin, is another common excipient. It can also be oxidized, but in the absence of metal ions or a metal surface, that will not cause a problem for the product shelf-life. Cellulose derivatives are other common excipients. One example is hydroxyl-propyl cellulose. Another embodiment uses xanthan gum, which is a nature-derived, high-molecular weight polysaccharide often used in skin product formulations to achieve the desired rheological characteristics. Colloidal silica as a viscosity modifier can be used at the lower pH if the silica is cationically modified. Sugar-based surfactants and other surfactants are known in the art as well.

Formulation Process

The process for making the final product formulation involves adding purified water, NaOCl and HAc reactants into air-free compartments within a container of the invention. Shelf-life of the formulations is thereby prolonged. The storage, and preparation processes are performed under air-free environmental conditions within the container.

Water, such as regular drinking water or deionized water, is provided. The water can be run through a purifying process one or more times, to remove organisms and ions. The air-free environment within the compartments can be made by degassing through reduced pressure. Additives may be included to achieve different viscosity, fragrance, or other properties.

The formulation may be titrated with, for example, NaOH and HAc, to a final pH of between 4.0 and 5.0, preferably about 4.76.

INCORPORATION BY REFERENCE

Any and all references and citations to other documents, such as patents, patent applications, patent publications, journals, books, papers, and web contents, which have been made throughout this disclosure, are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A system for storing and producing hypochlorous acid (HOCl), the system comprising:
   a container from which air has been purged, the container comprising a first compartment, a second compartment, a third compartment, and a fourth compartment, wherein the first compartment contains a compound that generates a hypochlorite anion (OCl—) in the presence of water, the second compartment contains a compound that generates a proton (H+) in the presence of water, and the third compartment contains water;
   a first one-way valve that permits fluid flow from the first compartment to the fourth compartment;
   a second one-way valve that permits fluid flow from the second compartment to the fourth compartment; and
   a third one-way valve that permits fluid flow from the third compartment to the fourth compartment.

2. The system of claim 1, wherein the first compartment contains water.

3. The system of claim 1, wherein the second compartment contains water.

4. The system of claim 3, wherein the second compartment contains at least one buffering agent.

5. The system of claim 4, wherein the water has a buffering capacity from about pH 3.5 to about pH 9.0.

6. The system of claim 4, wherein the buffering agent comprises acetic buffer or phosphate buffer.

7. The system of claim 1, wherein the fourth compartment contains water.

8. The system of claim 1, wherein the first compartment comprises walls of an opaque material.

9. The system of claim 1, wherein the first, second, and third one-way valves are configured to permit flow from the first, second, and third compartments into the fourth compartment in response to an increase in pressure within the first, second, and third compartments.

10. The system of claim 9, wherein the first, second, and third one-way valves are configured to permit flow from the first, second, and third compartments into the fourth compartment at a defined ratio in response to an increase in pressure within the first, second, and third compartments.

11. The system of claim 9, further comprising a member configured to increase pressure within the first, second, and third compartments upon user manipulation.

12. The system of claim 9, wherein the first, second, and third compartments comprise walls of a flexible material configured to allow an increase in internal pressure of the first, second, and third compartments in response to a force administered to an outside surface of the first, second, and third compartments.

13. The system of claim 1, further comprising a fourth one-way valve that permits fluid flow from the fourth compartment to an exterior of the container.

14. The system of claim 13, wherein the fourth compartment is configured to direct its contents to the exterior of the container in response to an increase in pressure within the fourth compartment.

15. The system of claim 14, further comprising a member configured to increase pressure within the fourth compartment upon user manipulation.

16. The system of claim 14, wherein the fourth compartment comprises walls of a flexible material configured to allow an increase in internal pressure of the third compartment in response to a force administered to an outside surface of the fourth compartment.

17. The system of claim 1, wherein the compound that generates a proton comprises an organic acid.

18. The system of claim 17, wherein the organic acid comprises acetic acid.

19. The system of claim 1, wherein the compound that generates a hypochlorite anion (OCl—) comprises sodium hypochlorite (NaOCl), Mg(OCl)2, or Ca(OCl)2.

20. The system of claim 1, configured to produce hypochlorous acid (HOCl) having a pH from about 4.5 to about 7.5 in the fourth compartment after introduction into the fourth compartment of the compound that generates a hypochlorite anion and the compound that generates a proton from the first and second compartments respectively.

21. The system of claim 1, wherein the container is a spray bottle.

* * * * *